United States Patent [19]
Atkins et al.

[11] Patent Number: 4,877,034
[45] Date of Patent: Oct. 31, 1989

[54] METHOD AND DEVICE FOR DETECTION OF TISSUE INFILTRATION

[75] Inventors: Judy M. Atkins; Benjamin J. Comfort, both of Hillsborough; Ralph A. Liebelt, Durham, all of N.C.

[73] Assignee: Smith & Nephew, Inc., Itasca, Ill.

[21] Appl. No.: 65,015

[22] Filed: Jun. 18, 1987

[51] Int. Cl.$^4$ ............................................... A61B 6/00
[52] U.S. Cl. .................................... 128/664; 128/665; 340/573
[58] Field of Search ............... 128/664, 665, 633, 634, 128/635, 640; 356/41; 340/540, 573, 603

[56] References Cited

U.S. PATENT DOCUMENTS

| | | | |
|---|---|---|---|
| 3,618,602 | 9/1971 | Shaw | 128/214 |
| 3,628,525 | 12/1971 | Polanyi | 128/2 |
| 4,010,749 | 8/1977 | Shaw | 128/214 |
| 4,029,085 | 6/1977 | DeWitt | 128/2 |
| 4,446,871 | 5/1984 | Imura | 128/63 |
| 4,447,150 | 5/1984 | Heinemann | 356/41 |
| 4,534,756 | 8/1985 | Nelson | 604/50 |
| 4,608,990 | 9/1986 | Elings | 128/633 |
| 4,647,281 | 3/1987 | Carr | 604/50 |
| 4,700,708 | 10/1987 | New, Jr. et al. | 128/633 |

OTHER PUBLICATIONS

Yoshiya et al., "Spectrophotometric Monitoring of Arterial Oxygen Saturation in the Fingertip", Med & Biol Eng & Comput. 1980, vol. 18 pp. 27–32.

Primary Examiner—Ruth S. Smith
Attorney, Agent, or Firm—McDermott, Will & Emery

[57] ABSTRACT

The invention comprises a noninvasive method and device that allows detection of tissue infiltration during the administration of fluids. In the invention, the tissue surrounding the site of intravenous injection is exposed to a plurality of wavelengths of electromagnetic radiation when no infiltration is occurring to determine a baseline reading. Changes in the relative levels of detected radiation at each wavelength as compared to the baseline reading indicate tissue infiltration.

10 Claims, 7 Drawing Sheets

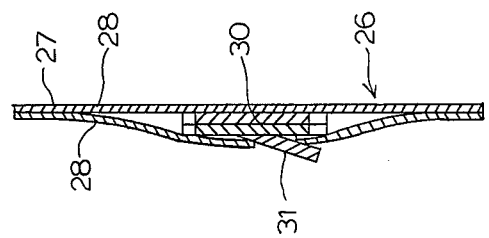
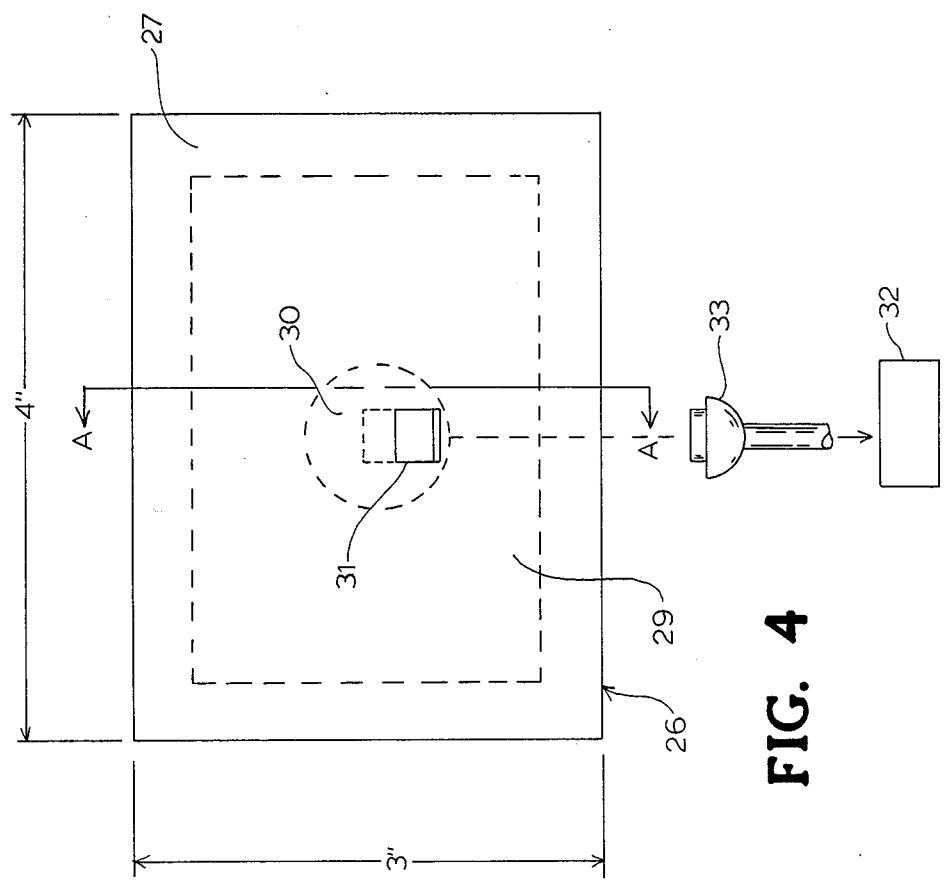
FIG. 5
FIG. 4

METHOD AND DEVICE FOR DETECTION OF TISSUE INFILTRATION

FIELD OF THE INVENTION

This invention relates to a noninvasive device and method for detecting tissue infiltration during intravenous administration of fluids.

BACKGROUND INFORMATION

A common problem encountered in intravenous fluid administration is the infiltration of the fluids into tissues near the point of entry of the catheter into the veins or arteries (vascular system). Infiltration is often due to patient movement and disruption of the vein or artery at the site of insertion of the catheter. This may lead to discoloration, discomfort and tissue destruction as well as lack of delivery of the intravenous fluids or drugs into the patient's system. Many surgical procedures including amputation may be required when certain drugs or fluids infiltrate the patient's tissues, causing necrosis. Permanent disfigurement and/or disability may be the result.

There are a number of devices and methods for detection of tissue infiltration during intravenous administration of fluids. These detection techniques include the measurement of the skin temperature in potential infiltration areas. These devices use temperature sensors for continuous monitoring of the skin temperature near the intravenous catheter. When colder intravenous fluids accumulate in tissue from infiltration the skin temperature falls. (See, for example, U.S. Pat. No. 3,618,602) The sensitivity of this technique may be enhanced by heating the skin around the catheter site so that tissue infiltration causes a greater temperature change. (U.S. Pat. No. 4,010,749) These devices do not work well when the administered fluid is not colder than the patient's skin. Additionally, when enough fluid has infiltrated to cause a temperature shift, edema and necrosis may already have occurred.

The most common method for detecting infiltration is by monitoring fluid delivery by a pump. In its simplest form, the drop frequency is monitored in the delivery chamber and an alarm is sounded if fluid delivery stops or falls short of the desired amount. More sensitive techniques include various methods for measuring specific changes in fluid delivery pressure as an index of infiltration. (See U.S. Pat. No. 4,534,756). Once infiltration has occurred and the equilibrium is disturbed in the infiltrated tissue the back flow pressure rises thus signaling infiltration. These devices cannot measure the initial event of infiltration, however, and studies have shown that they are probably not sensitive enough to signal an infiltration early enough to prevent irreversible changes in the tissue.

Another detection technique relies on clinical parameters including patient pain and actual visual inspection, by hospital personnel, of the area surrounding the catheter for signs of infiltration. To be effective this technique requires continual monitoring by trained hospital personnel.

Many of the problems of the prior art devices are overcome by the present invention which employs the change in the electromagnetic radiation-altering properties of tissue when infiltration occurs. Such a system has not been used to detect tissue infiltration with intravenous fluids or drugs. Electromagnetic radiation reflectance, transmission and intensity measurements have been used in other systems to measure components of living tissue such as oxygenated hemoglobin in the bloodstream (U.S. Pat. No. 4,446,871), bilirubin in the blood serum (U.S. Pat. No. 4,029,085), blood oxygen saturation (U.S. Pat. No. 3,628,525) and perfusion of blood into body tissues following surgery (U.S. Pat. No. 4,608,990).

One object of this invention is to provide a sensitive device whereby infiltration of intravenous fluids into tissue may be detected soon after the infiltration begins to prevent disastrous edema or necrosis.

Another object of the invention is to provide a noninvasive method and device for detection of tissue infiltration of any intravenous fluid or drug regardless of delivery temperature or pH.

Another object of the invention is to provide a device whereby tissue infiltration of fluids is detected automatically and appropriate measures taken to prevent further infiltration without continuous monitoring of the patient by health care personnel.

Another object of the invention is to provide a device for notifying hospital personnel remote from the patient by triggering an alarm upon infiltration.

Another object of the invention is to use a signal output from the invention to create an audio and/or visual alarm and to stop the fluid delivery from independent electronic intravenous delivery devices such as infusion pumps, controllers, or gravity intravenous sets.

Another object of the invention is to provide a device for detection of tissue infiltration that will require no new skills on the part of nursing personnel.

Another object of the invention is to provide a device for detection of tissue infiltration that will not be triggered excessively by ambient noise, light and temperature changes nor by patient activities.

Still other objects and advantages of the invention will be apparent to those of skill in the art after reading the following description of the preferred embodiment.

BRIEF DESCRIPTION OF THE DRAWINGS

FIG. 4 is a schematic drawing of the top of a second preferred embodiment of the invention.

FIG. 5 is a schematic drawing of a cross-section of a second preferred embodiment of the invention.

SUMMARY OF THE INVENTION

This invention makes possible the automatic monitoring of intravenous fluid administration, such that tissue infiltration by the intravenous fluids can be detected early enough to prevent irreversible tissue damage. It comprises a device and method for measuring changes in the relationship between two or more wavelengths of electromagnetic radiation traveling in tissue being infiltrated. Electromagnetic radiation from the device at two or more wavelengths ("incident radiation") is scattered, reflected or reemitted from the tissue surrounding the intravenous catheter tip and then detected ("detected radiation") by the device. Infiltrated fluid in the tissues causes a change in the proportion of incident radiation that becomes detected radiation. The magnitude of the change depends on the wavelength of electromagnetic radiation, the amount of infiltrated fluid, and the local properties of the tissue. Once the change occurs the information is relayed to trigger an alarm and appropriate devices to halt the delivery of fluid.

Description of the Preferred Embodiments

Figure 1:
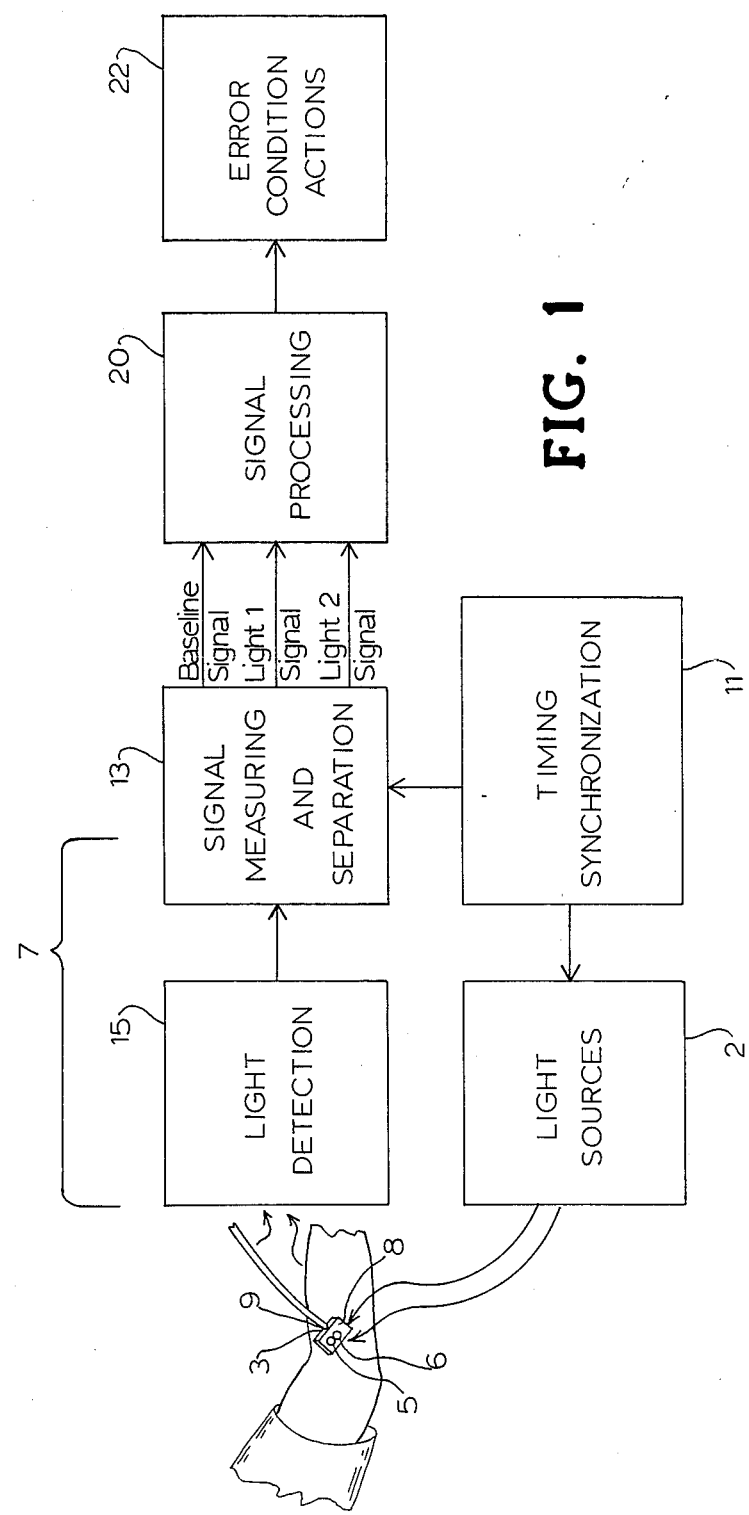
FIG. 1 is a block diagram of a preferred embodiment of the invention.
Figure 2:
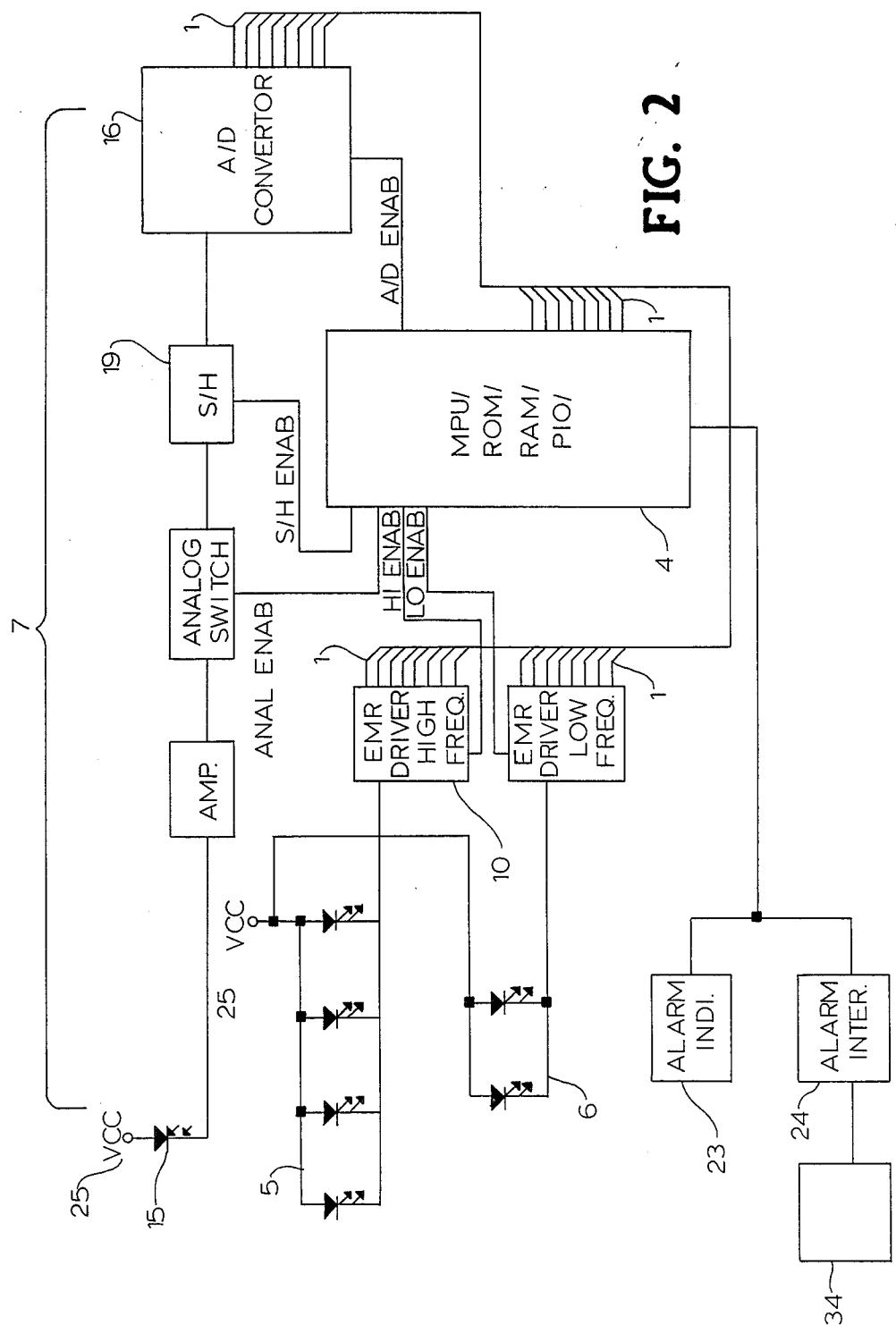
FIG. 2 is a detailed schematic drawing of a preferred embodiment of the invention.

FIG. 1 is a schematic drawing of a preferred embodiment of the invention. FIG. 2 schematically depicts the components of the preferred embodiment and the connections between the components in greater detail. Data lines 1 between the various electronic device allow information to be sent between them.

Figure 3A:
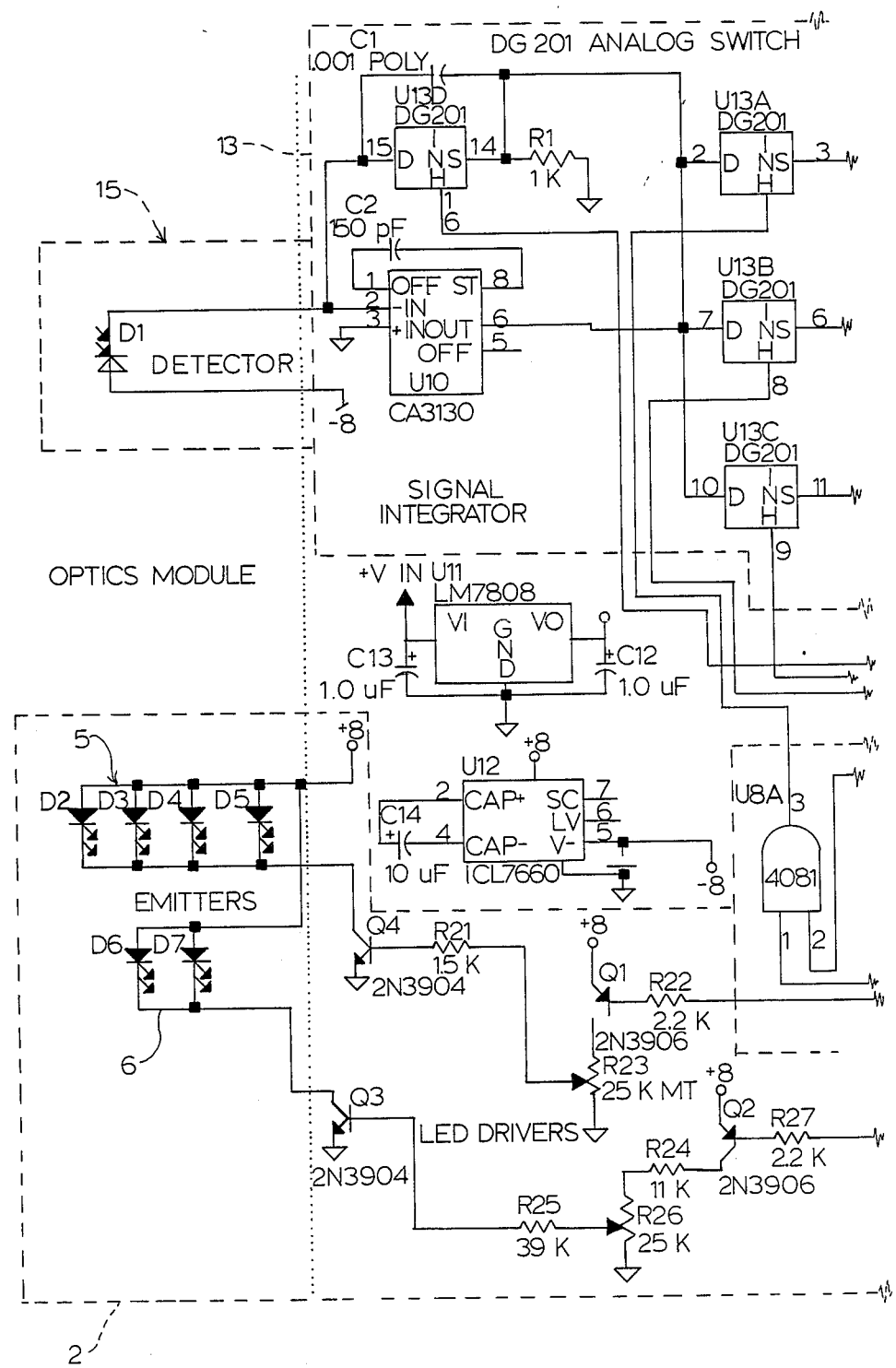
FIG. 3a, 3b and 3c are detailed schematic drawings of a working model of the invention.
Figure 3B:
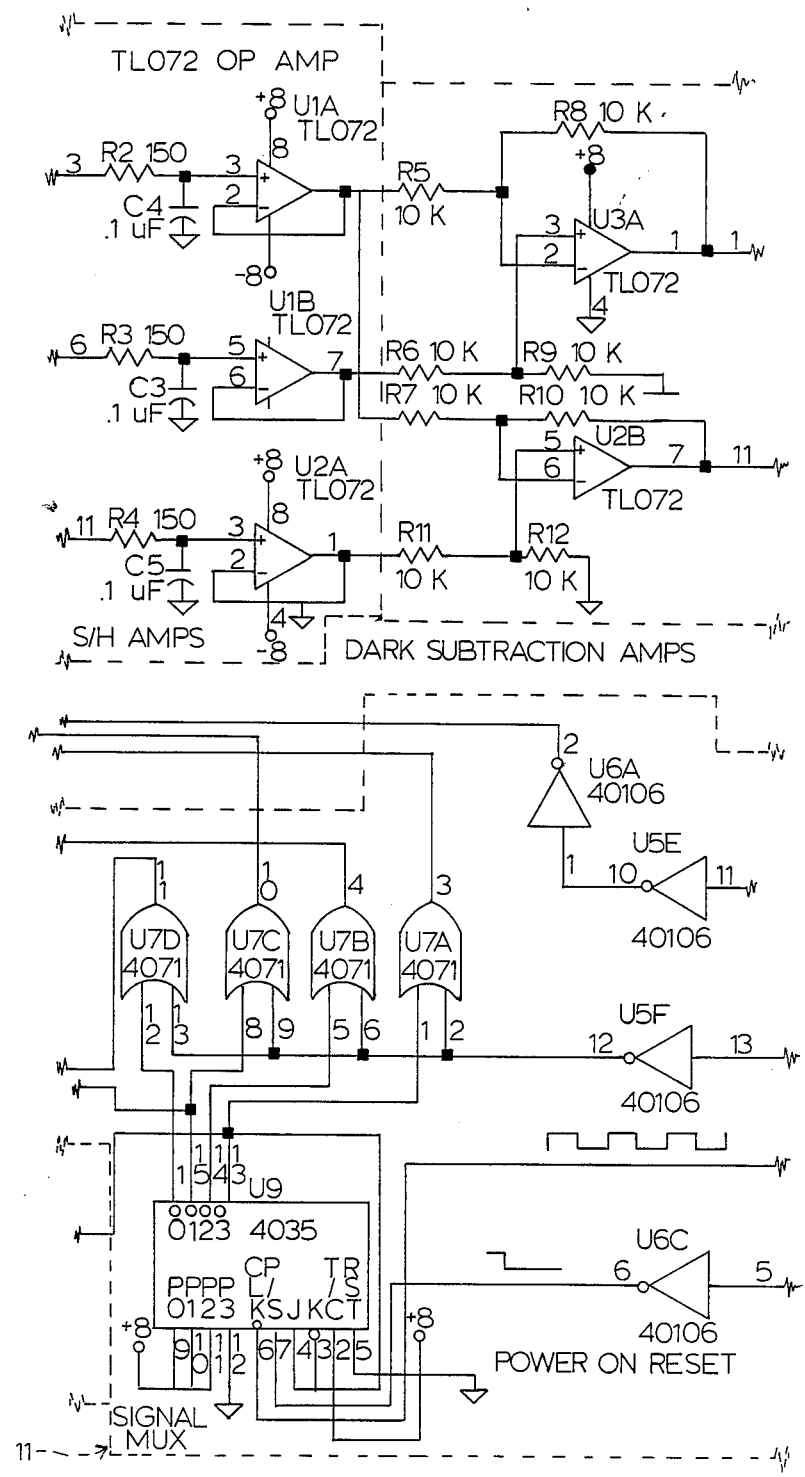
Figure 3C:
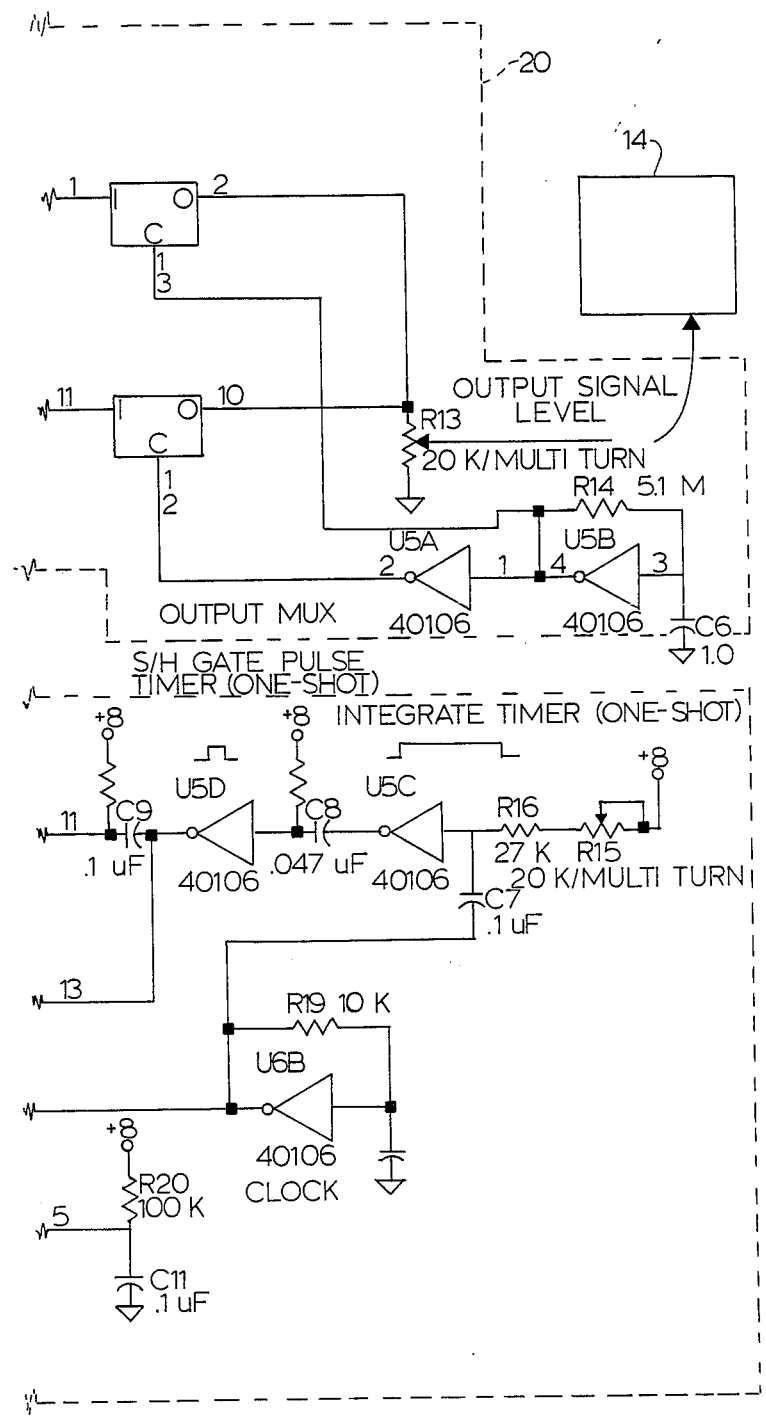
Figure 6:
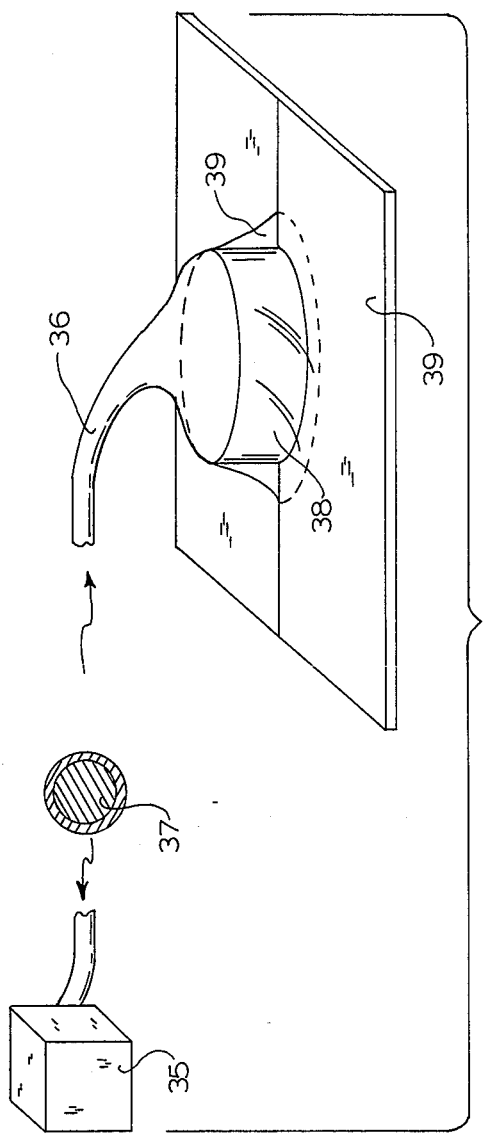
FIG. 6 is a schematic drawing of a third preferred embodiment of the invention.
Figure 7:
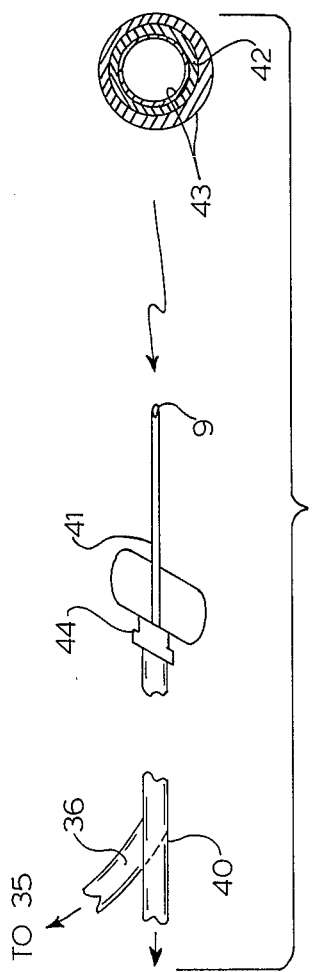
FIG. 7 is a schematic drawing of a fourth preferred embodiment of the invention.

FIGS. 3a, 3b and 3c show schematic drawings of a detailed monitoring circuit from a working model of this invention using generic parts and standard engineering notation. No microprocessor is used in this circuit. Signals are not coverted to digital form but remained in analog form. Measurements are recorded on an analog strip chart recorder 14. FIGS. 4 and 5 show a second preferred embodiment of the invention. FIGS. 6 and 7 show a third and fourth preferred embodiment of the invention utilizing fiber optic transmission of the incident and detected electromagnetic radiation.

In this invention, electromagnetic radiation sources 2 of two different wavelengths of radiation are used to direct electromagnetic radiation at the tissue surrounding the intravenous insertion site 3. The operation of the invention is controlled by one or more integrated circuits functioning essentially as a computer 4 as depicted by the central block in FIG. 2 (labeled MPU/ROM/RAM/PIO). The computer 4 includes a central microprocessor (MPU), a read only memory (ROM) that contains the instructions for the microprocessor, the read/write random access memory (RAM) that is used to hold data being processed by the microprocessor, and the programmable input output ports (PIO) to enable communication with other electronic circuits. The computer 4 has instructions and interfaces to control a high frequency electromagnetic radiation emitter or radiator 5, a low frequency electromagnetic radiation emitter or radiator 6, an electromagnetic radiation detection system 7, and an action component 22 including an alarm indicator 23 and alarm interface 24 (FIG. 2).

In the preferred embodiment, the two electromagnetic radiation emitters 5, 6 are light emitting diodes (LED) that emit visible red and infrared radiation and are placed in a patch 8 on the skin over the catheter tip 9. Electromagnetic radiation sources 2 of longer wavelengths such as visible electromagnetic radiation and infrared electromagnetic radiation have the advantage of increased penetration into the tissue to increase accuracy and sensitivity of the device. Less superficial areas are accessible with these wavelengths as well. The amount of radiation reflected, scattered and absorbed under particular conditions depends on the wavelength of the electromagnetic radiation and local tissue properties. The intensity of detected radiation at the two wavelengths changes when infiltration occurs and this change will be different for the different wavelengths. In other words, infiltration affects the alteration of detected electromagnetic radiation at one wavelength more than the other, allowing the difference to be used to indicate infiltration. Although infrared and visible red devices are utilized in the preferred embodiment description, it is possible to use other frequencies. Incorporated into the same patch 8 as the radiation sources 2 are sensor 30 of the electromagnetic radiation detection system 7, which in the preferred embodiment comprises a broad band electromagnetic radiation detector 15. The entire device may be incorporated in an adhesive bandage which simplifies placement and assures security of positioning.

The central processor in the computer 4 controls the intensity (signal output level) of the electromagnetic radiation sources 2, and their times of energizing, through electromagnetic radiation drivers 10. This is part of the timing synchronization circuit 11 (FIG. 1), which synchronizes the electromagnetic radiation flashes (on and off) of the two wavelengths and the measuring sequences. This multiplexing system first turns on one radiation emitter, then the second radiation emitter, measuring the particular detected radiation intensity with each. A baseline reading with neither emitter turned on completes the cycle.

The timing synchronization is comprised of standard digital logic circuitry. The timing of the electromagnetic radiation flashes may be rapid to detect problems more quickly; however, a rate of one cycle (a cycle consists of the first wavelength emission period, the second wavelength emission period, and a period of no radiation) per second is sufficient to detect tissue infiltration.

The detector 15 converts the radiation to an electrical signal. In the preferred embodiment a photodetector such as a silicon photo diode is used that measures the specific band of electromagnetic radiation wavelengths used in the radiation sources. Other photodetectors such as gallium arsenide, lead sulfide, germanium or photomultiplier tubes may also be used, as well as others for specific wavelengths of electromagnetic radiation.

Signal measuring and separation is accomplished in the preferred embodiment by means of an electrical signal measuring and separation circuit 13 that quantifies the electrical signal from the electromagnetic radiation detector 15. This includes an analog to digital converter 16 immediately following the sample and hold op-amp 19. Digital signal processing then does the ambient signal subtraction and the wavelength difference or ratio comparisons. Error condition logical outputs are based on this data. The central processor controls the electromagnetic radiation detection system 7, as determined by the program controlling the microprocessor. The microprocessor converts the received signals by controlling the analog to digital converter 16. The digital signal is "read" by the microprocessor in the computer 4 to monitor the system so that variations from standard values, caused by infiltration, are detected.

The signal processing component 20 in the computer 4 of the invention is comprised of microcode in the ROM of the computer 4 of the preferred embodiment of the invention. This monitoring process or signal processing enables the baseline signal reading (the generally small signal when there is only ambient radiation and no other electromagnetic radiation source is beamed at the skin) to be subtracted from the radiation detected from each of the electromagnetic radiation signals. The remaining values for each electromagnetic radiation source are then compared to each other. The difference between the readings for each wavelength at a particular time (or the ratio between the readings for each wavelength at the particular time) are compared to the analogous difference (or ratio) as determined when the administration of intravenous fluids is begun for a patient (time zero). Deviation in the difference or ratio of the electromagnetic radiation wavelength readings outside the normal system range indicates an intravenous infiltration problem or detachment of the patch 8 and intravenous catheter from the proper insertion site 3. The difference (or ratio) will not deviate outside of a limited range under normal, fault-free, conditions of intravenous fluid administration. The normal deviation range depends on the particular electrical components used in a system and not on the individual patient. The baseline is measured each cycle correcting for changes in ambient temperature, electromagnetic radiation and activity.

Logical output of the signal processing component 20 turns on when infiltration occurs and results in abnormal changes in the electromagnetic radiation wavelength difference or ratio. One embodiment of the signal processing component 20 of the invention includes an indicator when there are large variations in the baseline signal. This indicates skin patch 8 malpositioning. Additionally, the increased baseline measurement may cause the electromagnetic radiation sources 2 not to activate so that the system ceases measuring one or both wavelengths of electromagnetic radiation and triggers the action component 22 indicating a system malfunction.

At a minimum the action component 22 (FIG. 1) of the invention indicates that tissue infiltration is occurring when a signal is received from the signal processing component 20, for example, by turning on a red light or sounding an alarm. In the preferred embodiment, when the central processor detects an infiltration, it sends a signal to a local alarm indicator 23 and/or an alarm indicator at a remote location or a digital alarm interface 24. The alarm indicator 23 may be any combination of audible or visual signals. The alarm interface 24 may be connected to other patient monitor or control devices 34 such as an automated monitoring system or a device that controls fluid flow to the particular patient such that an alarm would allow the infusion means to the patient to be disconnected. Thus, if the intravenous administration system includes a pumping system, the action component 22 may also be connected to the pump control mechanism to deactivate the pump when infiltration is sensed.

The power source 25 for the invention may be standard electrical current, by battery or by other less traditional means such as photopower. Thus, in the embodiment in which all components are incorporated into the patch 8, the system could be powered by a battery or a photocell and the signal processing could send out an electrical, sound or light signal to a remote action system.

The invention may also be made as a disposable infiltration sensor 26 as shown in FIGS. 4 and 5. In this embodiment, the disposable invention comprises an extremely strong adhesive material around its outer edge 27 and one or more clear adhesive films or layers 28 in the interior area 29. The disposable infiltration sensor 26 has the electromagnetic radiation sources 2 and sensors 30 placed in the interior area 29, as well as a receptacle 31 in the interior area 29 to which the nondisposable control device 32 for intravenous infusion may be attached by such means as a plug 33. The clear adhesive layer or layers 28 allow light to travel from the electromagnetic radiation sources 2 to the skin and back to the sensors 30.

As shown in FIGS. 6, fiber optics can be used to provide a conduit for the transmission of electromagnetic radiation from the electromagnetic radiation sources 2 and to the detector 15 located in a remote analysis component 35 which also contains the other major components of other embodiments of the invention discussed above and shown in FIGS. 1 and 2. The fiber bundles 37 within a cable 36 are divided equally to allow simultaneous transmission of the incident and detected radiation. At a clear disc 38 placed over the catheter tip on the skin, the ends of the bundles 37 are placed topographically to allow adequate transmission and sampling of the electromagnetic radiation. The disc 38 is secured to the skin with a clear plastic adhesive 39. Analysis takes place at the remote analysis component 35 to avoid having wires and hardware in the patch itself.

Fiber optics can also be incorporated into the actual catheter 41 as shown in FIG. 7, eliminating a local external detection device and more accurately measuring the local environment at the catheter tip 9. All hardware is located at a remote analysis component 35. In this preferred embodiment inner fiber bundles 42 are incorporated in the catheter walls 43 in a topographic fashion to allow incident and detected electromagnetic radiation to be transmitted over different bundles 42 simultaneously. At the junction 44 of the intravenous tubing 40 and the catheter 41, the fiber bundles 42 are joined to form the cable 36 which then connects to the analysis component 35.

I claim:

1. A device for the detection of infiltration of intravenously delivered fluids into tissue surrounding an intravenous insertion site comprising radiation monitoring means for measuring changes in the relationship between a plurality of wavelengths of electromagnetic radiation traveling in said tissue upon the occurrence of tissue infiltration by said fluids in order to prevent tissue damage, said radiation monitoring means including:
   (a) a patch placed over said intravenous insertion site;
   (b) a plurality of electromagnetic radiation sources incorporated in said patch, said radiation sources directing electromagnetic radiation at said tissue;
   (c) radiation detection means additionally incorporated in said patch, said radiation detection means being capable of detecting said wavelengths of electromagnetic radiation and converting them to electrical signals; and
   (d) timing synchronization means electrically connected to said electromagnetic radiation sources, said timing synchronization means being capable of regulating the activation of said electromagnetic radiation sources.

2. The device of claim 1, wherein said radiation detection means is electrically connected to signal measuring and separation means, said signal measuring and separation means being capable of receiving said electrical signals from said radiation detection means and of quantifying said electrical signals.

3. A device for the detection of infiltration of intravenously delivered fluids into tissue surrounding an intravenous insertion site comprising radiation monitoring means for measuring changes in the relationship between a plurality of wavelengths of electromagnetic radiation traveling in said tissue upon the occurrence of tissue infiltration by said fluids in order to prevent tissue damage, said radiation monitoring means including:
(a) a patch placed over said intravenous insertion site;
(b) a plurality of electromagnetic radiation sources incorporated in said patch, said radiation sources directing electromagnetic radiation at said tissue;
(c) radiation detection means additionally incorporated in said patch, said radiation detection means being capable of detecting said wavelengths of electromagnetic radiation and converting them to electrical signals;
(d) timing synchronization means electrically connected to said electromagnetic radiation sources, said timing synchronization means being capable of regulating the activation of said electromagnetic radiation sources;
(e) signal measuring and separation means electrically connected to said radiation detection means, said signal measuring and separation means being capable of receiving said electrical signals from said radiation detection means and of quantifying said electrical signals; and
(f) signal processing means electrically connected to said signal measuring and separation means, said signal processing means being capable of comparing the quantified electrical signal measurements from said electromagnetic radiation sources and thereby detecting tissue infiltration.

4. The device of claim 3, further including an action component electrically connected to said signal processing means, said action component comprising an alarm means for generating an electrical signal, said alarm means being electrically activated upon the occurrence of tissue infiltration by said fluids.

5. The device of claim 4, wherein the electromagnetic radiation sources comprise infrared and red-light emitting diodes.

6. The device of claim 4, wherein said alarm means is electronically connected to a fluid control means, said fluid control means curtailing said intravenous fluid delivery upon receiving said electrical signal from said alarm means.

7. The device of claim 3, wherein said radiation monitoring means comprises fiber optic means for transmitting said electromagnetic radiation to said radiation detection means.

8. A method for detecting an area of tissue infiltration by intravenously delivered fluids comprising the steps of:
(a) alternately exposing said area to a plurality of wavelengths of electromagnetic radiation and then to no electromagnetic radiation other than ambient light; and
(b) monitoring the changes in the relationship between the amounts of detectable electromagnetic radiation of each wavelength over time as compared to the relationship between the amounts of detectable electromagnetic radiation of each wavelength in the absence of tissue infiltration at the time when the intravenous fluid delivery is commenced.

9. The method of claim 8, further comprising the step of generating an alarm signal when the relationship between the amounts of detectable electromagnetic radiation at each wavelength differs from the relationship between said amounts in the absence of tissue infiltration.

10. The method of claim 9, further comprising the step of activating an intravenous fluid control device to curtail said intravenous fluid delivery in response to said alarm signal.

* * * * *